United States Patent [19]

Hideshima

[11] Patent Number: 4,996,990

[45] Date of Patent: Mar. 5, 1991

[54] AIR-PUFF TONOMETER

[75] Inventor: Masayuki Hideshima, Tokyo, Japan

[73] Assignee: Tokyo Kogaku Kikai Kabushiki Kaisha, Japan

[21] Appl. No.: 231,293

[22] Filed: Aug. 12, 1988

[30] Foreign Application Priority Data

Aug. 12, 1987 [JP] Japan .................................. 62-201135
Sep. 14, 1987 [JP] Japan .................................. 62-230326

[51] Int. Cl.$^5$ ................................................ A61B 3/16
[52] U.S. Cl. ..................................... 128/648; 128/652
[58] Field of Search ................................. 128/648–652, 128/745, 682; 73/81

[56] References Cited

U.S. PATENT DOCUMENTS

| | | | |
|---|---|---|---|
| 3,232,099 | 2/1966 | Motchenbacher | 128/648 |
| 3,538,754 | 10/1970 | Grolman et al. | 128/648 |
| 4,172,447 | 10/1974 | Bencze et al. | 128/648 |
| 4,724,843 | 2/1988 | Fisher | 128/648 |
| 4,817,620 | 4/1989 | Katsuragi et al. | 128/648 |
| 4,825,873 | 5/1989 | Kohayakawa | 128/648 |
| 4,832,039 | 5/1989 | Perry et al. | 128/682 |
| 4,860,760 | 8/1989 | Miyawaki et al. | 128/682 |

Primary Examiner—Lee S. Cohen
Assistant Examiner—John D. Zele
Attorney, Agent, or Firm—Finnegan, Henderson, Farabow, Garrett & Dunner

[57] ABSTRACT

An air-puff tonometer, in which a puff of compressed air is blown out through a nozzle (N) toward the cornea of a subject eye (H), said compressed air being produced by energizing with an electric current a piston drive, which when thus driven compresses the air within a cylinder (5) in which the piston is mounted. The tonometer is provided with: pressure detector (11) for detecting the pressure within the cylinder (5); and current control (12, 14) for comparing a pressure signal (Vp) outputted from said pressure detector (11) with a predetermined reference signal (Vt) and for controlling the current supplied to said piston drive in such a manner that the difference between said pressure signal and said reference signal will be reduced.

The air-puff tonometer so constructed will allow air within the cylinder thereof to be compressed in accordance with a predetermined pressure-time characteristic curve in spite of any change occurring in the clearance between the piston and the cylinder walls.

Other tonometers are also disclosed which are arranged to detect the actual air-puff pressure at the moment the cornea flattens.

6 Claims, 7 Drawing Sheets

AIR-PUFF TONOMETER

FIELD OF THE INVENTION

The present invention relates to an air-puff tonometer which directs a puff of compressed air to the eye through a nozzle so as to measure the intraocular pressure.

BACKGROUND OF THE INVENTION

A prior art air-puff tonometer of such type is shown in FIG. 7.

The tonometer shown in FIG. 7 has a rotary solenoid 1 which acts as means for driving a piston 3. An arm 2 of the rotary solenoid 1 is connected to a piston rod 4 integral with the piston 3. The piston 3 is mounted in a cylinder 5 in which a compression chamber 6 is defined. The chamber 6 is connected to a nozzle (not shown) which is used to direct a puff of compressed air supplied from the compression chamber 6. The arm 2 will be turned in the counterclockwise direction by energizing the rotary solenoid, and will be turned back to the initial position by the elastic action of a spring (not shown) upon deenergization of the solenoid 1.

As the arm 2 is turned in the counterclockwise direction by the rotary solenoid 1, the piston 3 is moved upward with the piston rod 4, whereby air within the compression chamber 6 is compressed and thus driven against the subject eye through said nozzle.

To blow out a puff of compressed air, a strong force must be applied to the piston 3 and therefore an intense electric current must be supplied to the rotary solenoid 1 through a constant-current circuit 9. The intense current is generated by discharging a capacitor 8 in a short time. The capacitor is charged by a charging circuit 7.

The constant-current circuit 9 regulates the intense current to a constant current, which is supplied to the rotary solenoid 1, whereby the solenoid 1 will drive the piston 3 with a force of predetermined strength. The pressure of the air puff is thus adjusted to a constant value.

A prior art air-puff tonometer disclosed in Japanese patent publication No. 38437/1979 is provided with an optical transmitter system (not shown) for directing a detection light beam to the cornea of a subject eye, and with an optical receiver system (not shown) for receiving the detection light which was emitted from the transmitter and reflected by the cornea. This prior art apparatus directs a flow of fluid to the cornea of the subject eye. The cornea will be deformed from convex to flat and then to concave as the pressure of the fluid flow increases. Further, the cornea will then be deformed from concave to flat, and will eventually restore its original convex form as the fluid pressure decreases. The air-puff tonometer operates based on such deformation of the cornea.

The optical transmitter and the optical receiver are set such that the amount of light received by the receiver will be maximum when the cornea of the subject eye is flat. The compressing of air is performed such as to achieve a predetermined pressure-time characteristic curve A shown in FIG. 8. Since the time required for the deformation or restoration of the cornea is correlated to the intraocular pressure, it can be determined using such time as the variable. In accordance with the diclosure of the above-mentioned Japanese patent publication No. 38437-1979, the time $t_1$ is measured which is the interval of time from the initiation of the fluid flow according to the pressure-time characteristic curve A until the cornea is deformed from convex to flat, and the thus measured time $t_1$ is converted to the corresponding intraocular pressure. In fact, the time $t_1$ is measured as the time interval until the intensity of light reflected from the cornea and received by the receiver system becomes maximum. The conversion of the time $t_1$ is as follows: the pressure value of the fluid Pe at the point of time $t_1$ is determined on the basis of the fluid pressure-time characteristic curve A and such value Pe is considered to be equal to the intraocular pressure. In accordance with such prior art, the intraocular pressure can also be determined using a measured time interval between a first time point $t_1$ at which the cornea becomes flat while being deformed inwardly by the fluid flow directed thereto, and a second time point $t_2$ at which the cornea becomes flat again while being restoring its original convex form. In FIG. 8, character B designates a characteristic curve of the amount of received light versus time, while $P_{max}$ designates the maximum pressure value of the fluid.

The first mentioned prior art air-puff tonometer however has a problem in that a change in the clearance between the piston 3 and the cylinder walls due to abrasion will cause a corresponding change in the pressure of air compressed in the cylinder 5 since the air is compressed by the piston 3 being driven with a predetermined constant thrust produced by the constant current supplied from the constant-current circuit 9 to the rotary solenoid 1. Since said change in the clearance will cause a corresponding change in the pressure-time characteristic of the air puff blown out through the nozzle, significantly large errors may be included in the measurements taken by a tonometer which determines the intraocular pressure on the basis of the measured time interval between the moment the air puff occurs and the moment the cornea flattens.

The second mentioned prior art air-puff tonometer disclosed in Japanese patent publication No. 38437/1979 also has a problem in that it does not actually measure the air puff pressure at the moment the cornea flattens. Thus, it is necessary for such tonometer that the air-puff pressure should vary following the pressure-to-time characteristic curve A of FIG. 8. Therefore, any deviation of the actual air-puff pressure from the reference pressure-time characteristic curve A will immediately cause a corresponding error in the value of the intraocular pressure thus determined by the tonometer. The prior art tonometers thus are not ones which allow for improvent in the accuracy of measurent.

SUMMARY OF THE INVENTION

A first object of the present invention is therefore to provide an air-puff tonometer in which air within the cylinder thereof can be compressed in accordance with a predetermined pressure-time characteristic curve in spite of any change occurring in the clearance between the piston and the cylinder walls.

A second object of the present invention is to provide an air-puff tonometer which allows for further improvement in the accuracy of measurement of the intraocular pressure.

A third object of the present invention is to provide an air-puff tonometer which can detect the actual pressure of the air puff at the moment the cornea flattens to thereby accurately determine the intraocular pressure, and which can be of a simple construction which can be manufactured at low costs.

To achieve the first object, the air-puff tonometer according to one aspect of the present invention blows a puff of compressed air out through a nozzle toward the cornea of a subject eye. The compressed air is produced by energizing with an electric current a piston drive means for driving a piston which when thus driven compresses the air within a cylinder in which the piston is mounted. The tonometer is further provided with:

pressure detecting means for detecting the pressure within said cylinder; and current control means for comparing a pressure signal outputted from said pressure detecting means with a predetermined reference signal and for controlling the current supplied to said piston drive means in such a manner that the difference between said pressure signal and said reference signal will be reduced to zero.

To achieve the second and third objects, an air-puff tonometer according to another aspect of the present invention blows a puff of compressed air through a nozzle toward the cornea of a subject eye. The compressed air is produced by energizing with an electric current a piston drive means for driving a piston which when thus driven compresses the air within a cylinder in which the piston is mounted. The tonometer also include means provided for detecting the flattening of the corea caused by the air puff directed thereto, and:

pressure detecting means for detecting the pressure of the air puff at the moment said flattening detecting means detects the flattening of the cornea.

To achieve the second and third objects, the air-puff tonometer according to a further aspect of the present invention is characterized in that said pressure detecting means comprises:

a pressure detecting circuit for detecting the pressure of air blown out through the nozzle and for producing a voltage which corresponds to the detected pressure;

a sampling/holding circuit for holding the voltage produced by said pressure detecting circuit at the moment said flattening detecting means detects the flattening of the cornea; and an analog-to-digital converter for analog-to-digital converting the voltage held by the sampling/holding circuit.

DESCRIPTION OF THE PREFERRED EMBODIMENTS

Figure 7:
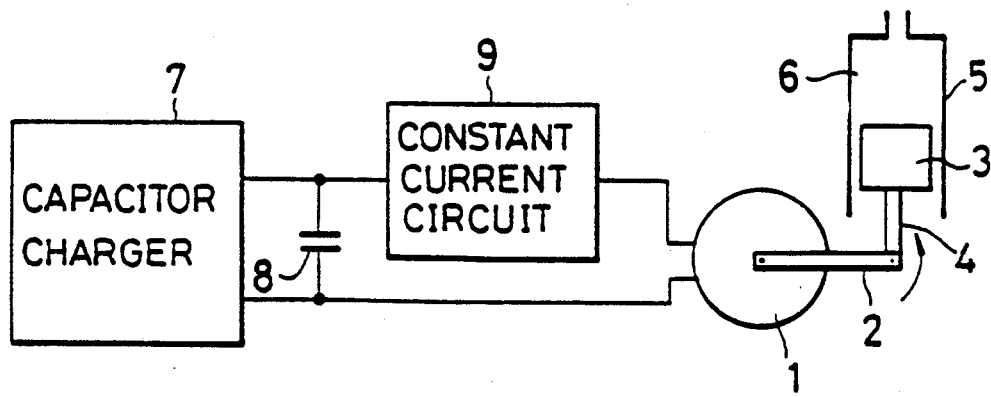
FIG. 7 is an illustration schematically showing the construction of a prior art air-puff tonometer.
Figure 8:
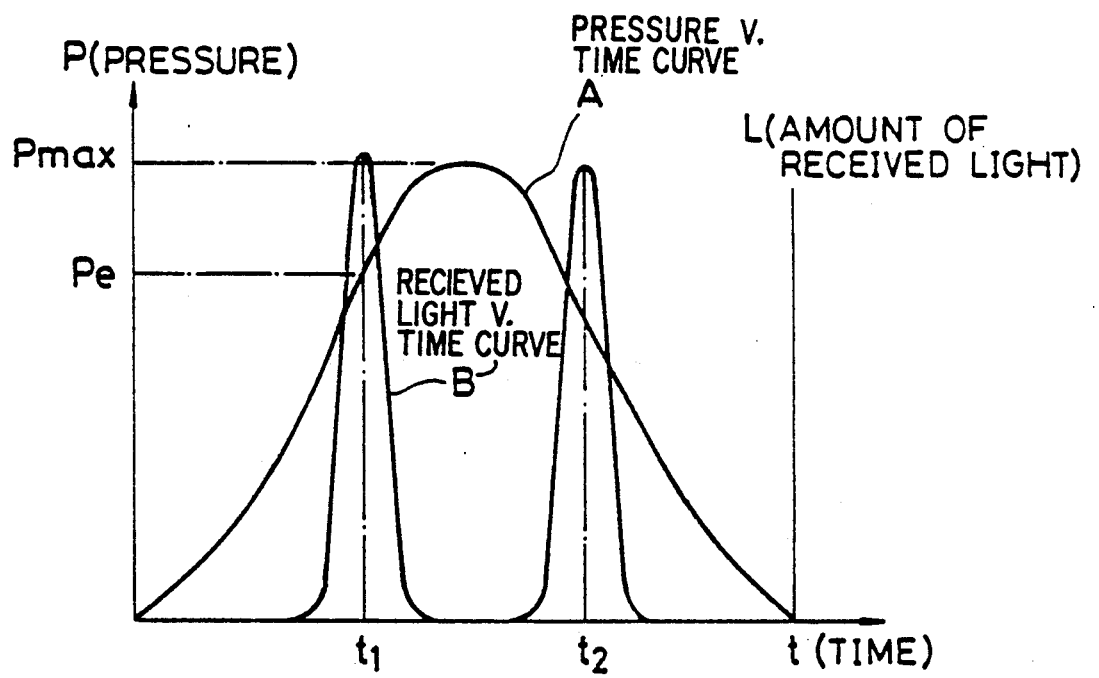
FIG. 8 is a graph representing a characteristic curve which accounts for the disadvantage of the prior art apparatus.

Several embodiments of the present invention to achieve the above-mentioned objects will be described with reference to the accompanying drawings. Those elements which are shown in figures other than FIG. 7 and which have equivalents in FIG. 7 are designated by equivalent or identical reference characters and will not be described again.

FIRST EMBODIMENT

Figure 1:
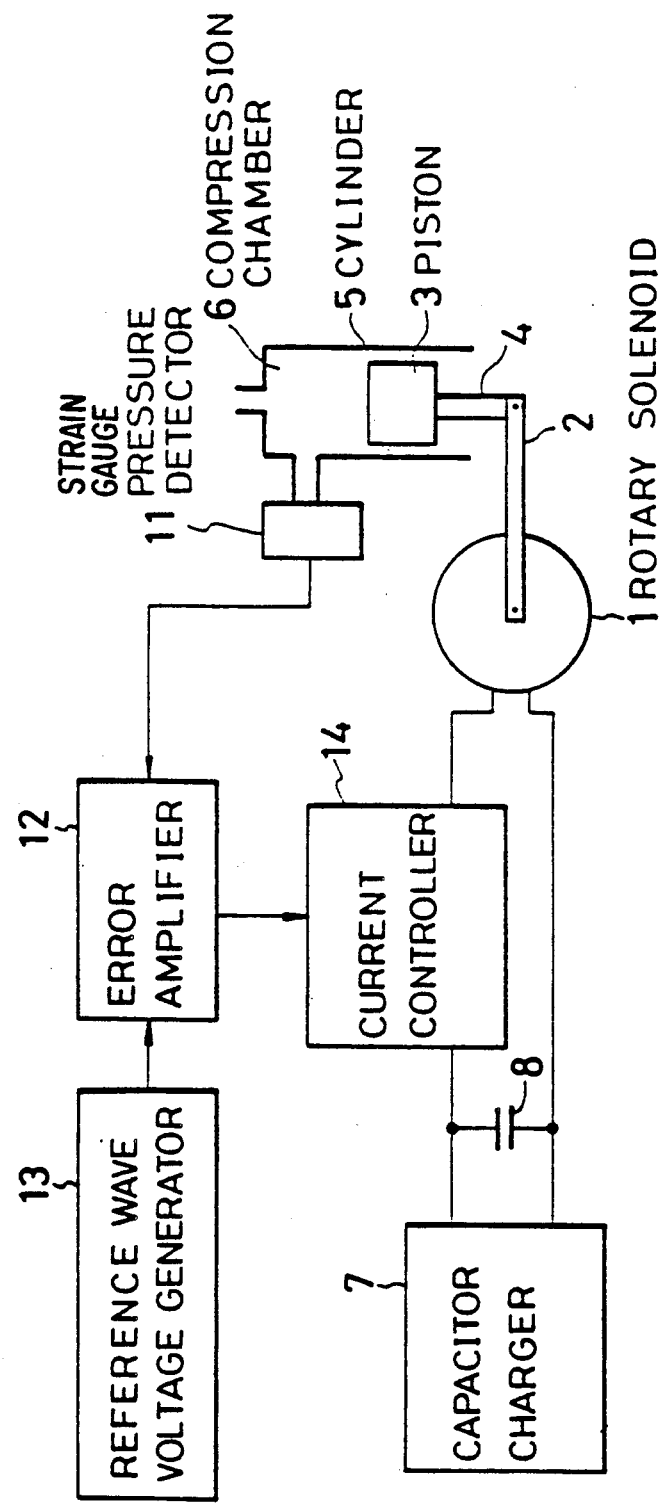
FIG. 1 is a block diagram showing the control system of a first embodiment of the air-puff tonometer according to the present invention.

FIG. 1 is a block diagram showing the control system of an air-puff tonometer according to the present invention in which 11 designates a pressure detecting circuit which detects the pressure in a compression chamber chamber 6 within a cylinder 5 and produces a voltage, i.e. pressure signal, corresponding to the detected pressure, and which may be constituted, for example, by a strain-gauge type pressure detector. An error amplifying circuit 12 amplifies the difference between the voltage of the pressure signal produced by the pressure detector 11 and a reference wave voltage signal produced by a reference wave voltage signal generating circuit 13 to be described later. The amplifier 12 may be constituted by a differential amplifier, for example.

The reference wave voltage generator 13 produces a reference wave voltage signal having the wave form of the pressure signal which is to be produced by the pressure detector 11 when the pressure in the compression chamber 6 within the cylinder 5 varies in an ideal manner during a compressing stroke. To compensate for the delay time T of the overall system during the feedback control, the reference wave voltage generator 13 begins to produce the output reference wave voltage signal at a time point $t_0$ which preceeds by the delay time T the time point $t_R$ at which the piston 3 begins to rise, as shown in FIG. 2(A).

A current control circuit 14 controls a current supplied from a capacitor 8 to a rotary solenoid 1 in such a manner that the amplified-error signal from the error amplifier 12 will be reduced to zero. The current controller 14 may be constituted, for example, by a power transistor whose base receives the amplified-error signal to control the current flowing through the collector thereof. The error amplifier 12, reference wave voltage generator 13 and current controller 14 form in combination a current controlling means.

The operation of the air-puff tonometer will now be described.

Figure 2:
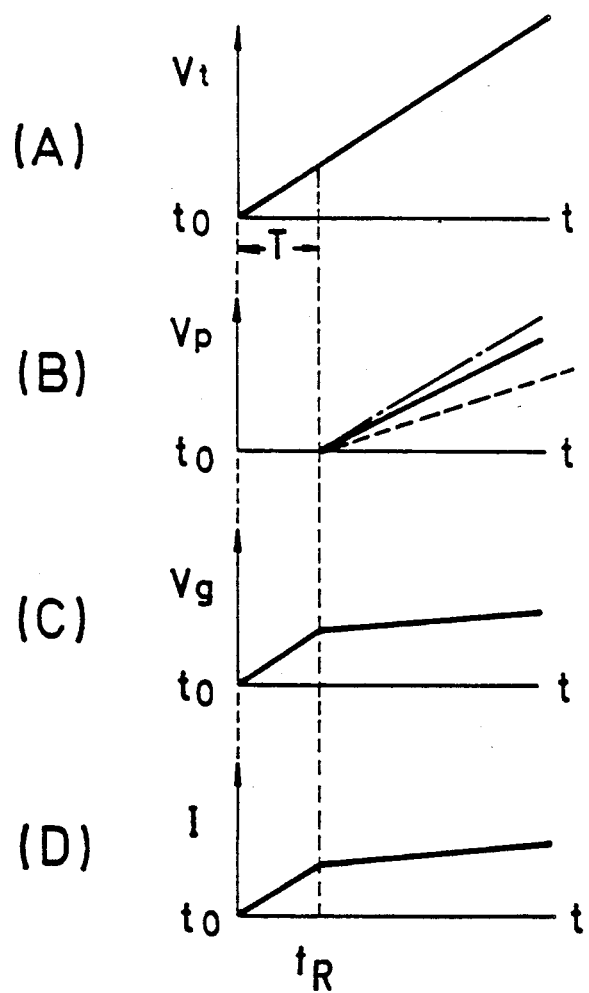
FIG. 2 shows graphs (A), (B), (C), and (D) representing the relation between the pressure within a compression chamber and signals produced in several circuits in the control system of FIG. 1.

When the volume of the compression chamber 6 within the cylinder 5 is not compressed at all and the piston 3 is in the position shown in FIG. 1, the capacitor 8 is charged by a capacitor charging circuit 7, and the reference wave voltage generator 13 will begin to produce a linear reference wave voltage signal Vt at time point $t_0$ as shown in FIG. 2(A). Then, since the value of the pressure signal Vp produced by the pressure detector 11 is zero, the error signal Vg produced by the error amplifier 12 is a voltage linearly proportional to the reference wave voltage signal Vt, which is supplied to the current controller 14 which in turn will allow a current to be released from the capacitor to the rotary solenoid 1.

The rotary solenoid 1 will begin to operate at time point $t_R$ which coincides with the delay time T after the moment to at which such current begins to flow through the rotary solenoid 1 to raise the piston 3. The pressure detector 11 will produce the pressure signal Vp which is linearly proportional to the pressure within the compression chamber, as shown in FIG. 2(B). The current controller 14 will supply a current the intensity of which is linearly proportional to the voltage of the error signal Vg as shown in FIG. 2(D), so that the error signal Vg can be reduced to zero. In other words, the rotary solenoid 1 receives a current which is adjusted such that the pressure signal Vp will become equal to the reference wave voltage signal Vt. The air in the compression chamber 6 within the cylinder 5 will thus be compressed by the piston 3 such that the actual pressure in the chamber 6 will change following the ideal pressure curve, whereby an air puff of predetermined pressure can be achieved.

If however the compression in the compression chamber 6 has become insufficient due to a change in the clearance between the piston 3 and the cylinder walls 5 which may be caused by abrasion, and accordingly the pressure signal Vp produced by the pressure detector 11 changes as the broken line shown in FIG. 2(B), then the difference between the pressure signal Vp and the reference wave voltage signal Vt produced by the reference wave voltage generator 13 will become larger and accordingly the voltage of the error signal Vg produced by the error amplifier 12 will become higher, so that the current controller 14 will intensify the current supplied to the rotary solenoid 1, whereby the piston 3 will be pushed upward with an intensified force and thus the air in the compression chamber 6 can be compressed to achieve the predetermined pressure.

If, on the contrary, the compression in the compression chamber becomes excessive due to a change in the clearance between the piston 3 and the cylinder walls 5, and accordingly the pressure signal Vp produced by the pressure detector 11 changes as the chain line shown in FIG. 2(B), then the difference between the pressure signal Vp and the reference wave voltage signal Vt produced by the reference wave voltage generator 13 will become smaller and accordingly the voltage of the error signal Vg produced by the error amplifier 12 will become lower, so that the current controller 14 will lessen the current supplied to the rotary solenoid 1, whereby the piston 3 will be pushed upward with a lessened force and thus the air in the compression chamber can be compressed to achieve the predetermined pressure.

The current controller 14 will thus automatically control the current supplied to the rotary solenoid 1 so as to adjust the compressing force exerted by the piston 3, whereby any change in the clearance between the cylinder walls 5 and the piston 3, which can occur due to abrasion and may otherwise affect the compressing operation, can automatically be compensated for and the air within the compression chamber 6 can be compressed to the predetermined pressure.

The automatic control of the compressing force is effected in any case where something will affect the quality of the compressing operation. For example, the automatic control is also effected when the rotary solenoid 1 has deteriorated, and a similar effect can be achieved. A more accurate measurement can be achieved if it is applied to an air-puff tonometer of the type which determines the intraocular pressure on the basis of the pressure of the air puff at a location immediately adjacent to the cornea, which pressure is estimated from the measurement of the pressure within the cylinder 5.

Further, if the error amplifier 12 is provided with "P, I, D" (proportionality, integration, differentiation) characteristics, it is possible to achieve an actual pressure variation within the compression chamber 6 during the compressing stroke which is very close to the ideal pressure variation. Also, the error amplifier 12 can be arranged to give an alarm when the actual pressure in the compression chamber 6 has become different from the ideal by a predetermined amount, whereby the operator can be made aware that something is wrong, for example, concerning the current supplied to the rotary solenoid 1, or the inner walls of the cylinder 5.

In the above-described embodiment, the piston 3 is driven with a force which is proportional to an electric current. The present invention however may be implemented otherwise than with such an arrangement. For example, the piston may be driven with a force which is proportional to a voltage.

SECOND EMBODIMENT

Figure 3:
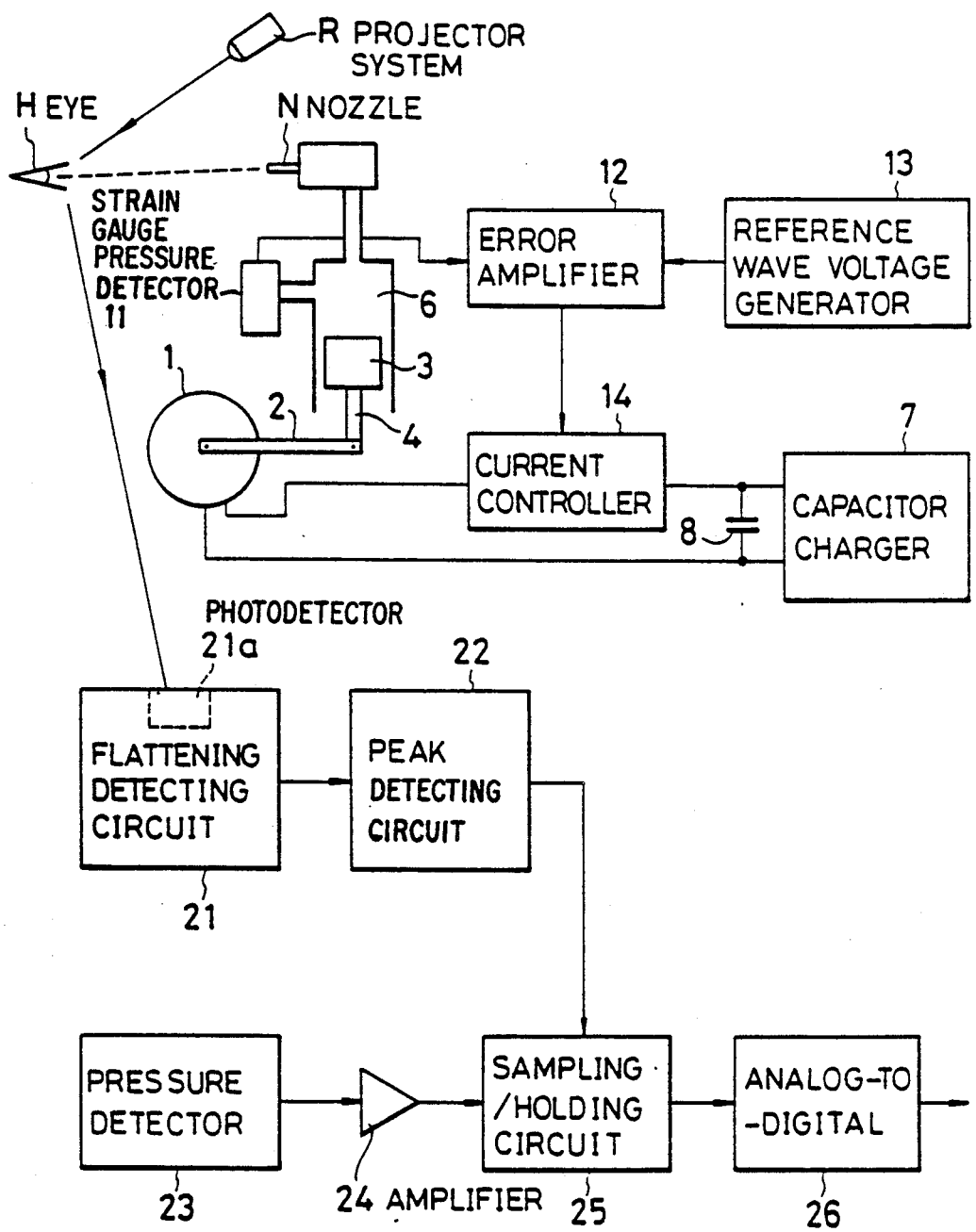
FIG. 3 is a block diagram showing a second embodiment of the air-puff tonometer.

FIG. 3 is a block diagram showing the arrangement of another embodiment of the air-puff tonometer which achieves the previously mentioned first and third objects of the present invention. Those elements which have equivalents in the embodiment shown in FIG. 1 are designated by identical reference characters and will not be described. In FIG. 3, character R designates a light projecting system which projects a beam of infrared radiation to the subject eye H; N designates a nozzle for directing an air flow toward the eye H; 21 designates a flattening detecting circuit for producing a signal which corresponds to the form of the cornea of the eye H. The flattening detecting circuit 21 comprises a photodetector 21a which receives the infrared radiation reflected from the cornea; the photodetector is set such that the amount of the thus received radiation becomes maximum at the moment the cornea flattens.

Figure 4:
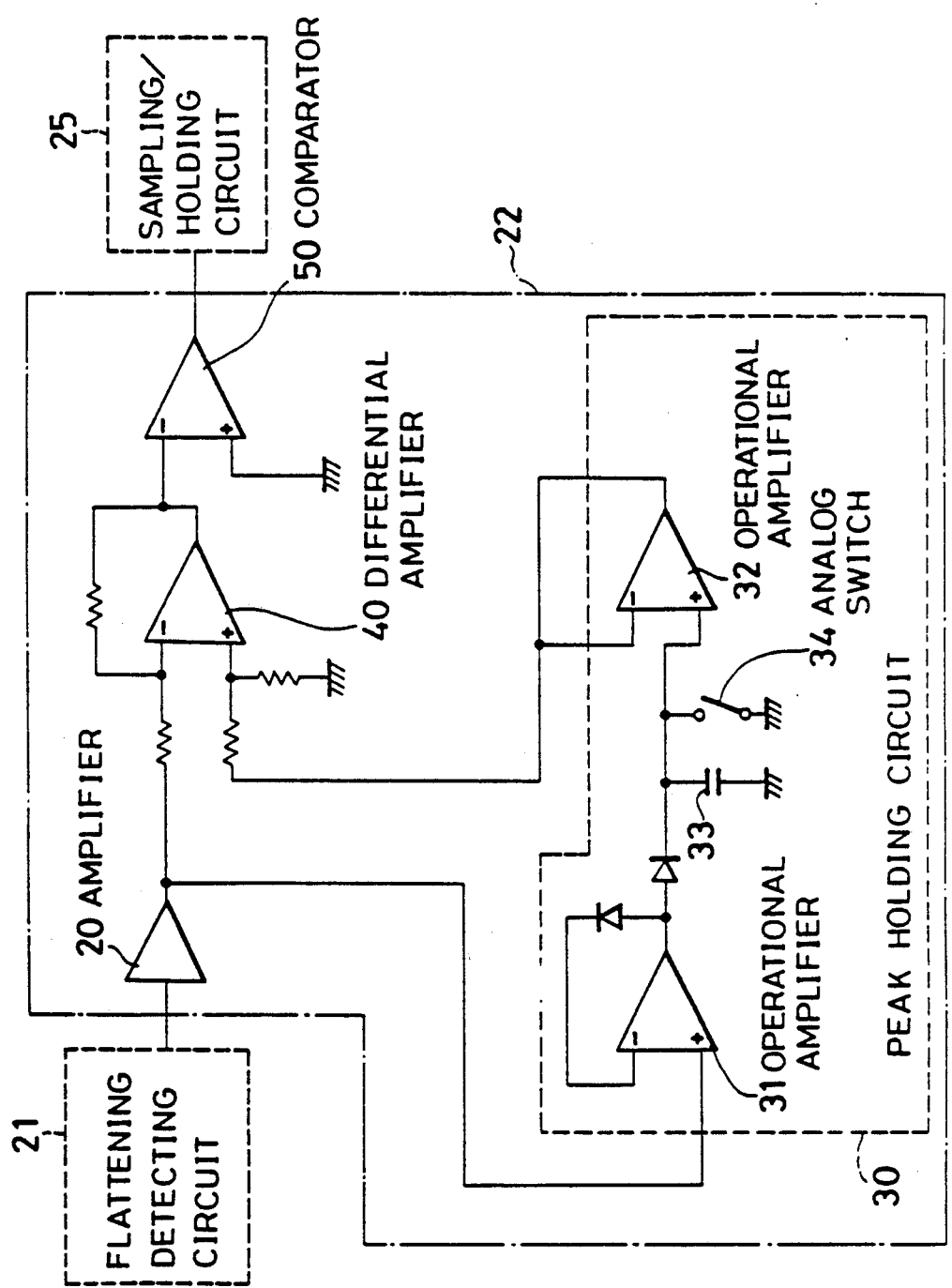
FIG. 4 is a circuit diagram specifically showing a peak detecting circuit.

A peak detecting circuit 22 provides an output signal whose value is the logic high level when the value of the output from the flattening detecting circuit 21 exceeds the maximum output value which the flattening detecting circuit has produced until then. FIG. 4 shows the components of the peak detector 22, which include: a peak holding circuit 30 for holding the peak value of the amplified signal from a buffer amplifier 20; a differential amplifier 40 for amplifying the difference between the peak signal from the peak holding circuit 30 and the amplified signal from the buffer amplifier 20; and a comparator 50 for producing an output signal whose value is the logic high level when the signal value from the differential amplifier 40 is negative, i.e. when the amplified signal from the buffer amplifier 20 is higher than the amplifier signal held by the peak holding circuit 30.

The peak holding circuit 30 comprises: operational amplifiers 31 and 32; a capacitor 33 for holding the peak voltage of the amplified signal from the buffer amplifier 20; and an analog switch 34 which is used, before the initiation of a measuring process, to release the charge which has been accumulated in the capacitor 33 during the previous measuring process. The flattening detecting circuit 21 and the peak detecting circuit 22 constitute in combination the means for detecting the flattening of the cornea.

In FIG. 3, 23 designates a pressure detector separate from the pressure detector 11 for producing a pressure signal of a voltage corresponding to a the pressure of the air blown against the cornea of the subject eye H; 24 designates an amplifier for amplifying the pressure signal; 25 designates a sampling/holding circuit for taking and holding a sample of the pressure signal from the amplifier 24 when the value of the output signal from the peak detector 22 is the logic high level; and 26 designates an analog-to-digital converter for analog-to-digital converting the voltage held by the sampling/holding circuit 25. The pressure detector 23 and the sampling-/holding circuit 25 consitute in combination the pressure detecting means.

The operation of the above-described air-puff tonometer will now be described.

Firstly, the analog switch 34 of the peak holding circuit 30 is closed for a predetermined time so as to release the electric charge which has been accumulated in the capacitor during the preceding measuring process. Then, the projector system R is operated to project a beam of infrared radiation to the subject eye while a flow of air is blown through the nozzle N against the eye. The pressure of the air flow increases as time passes. The air flow will progressively dent the cornea of the subject eye H. The flattening detecting circuit 21 will produce a signal $V_F$ whose value depends on the form of the cornea and becomes maximum at the moment $t_F$ when the cornea becomes flat, as shown in FIG. 5(A). The peak detecting circuit 22 will produce a signal whose value is the logic high level when the signal level from the flattening detecting circuit 21 is higher than the maximum signal level produced until then. Specifically, as shown in FIG. 5(B), the signal level from the peak detecting circuit 22 is high during the period between $t_0$ and $t_{m1}$ and during the period between $t_{m2}$ and $t_F$.

Figure 5:
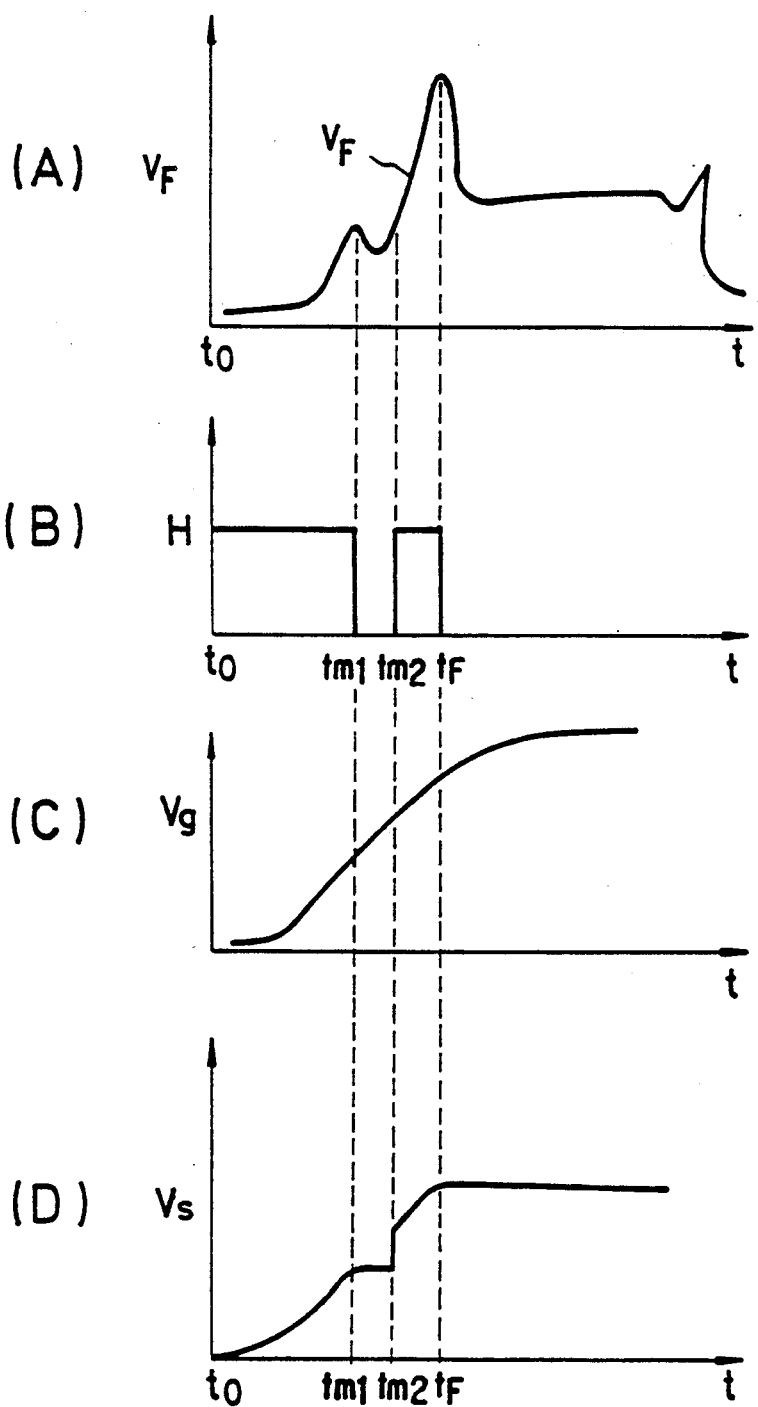
FIG. 5 shows graphs (A), (B), (C) and (D) representing output signals from several circuits.

Meanwhile, the pressure detector 23 will produce a pressure signal Vg which corresponds to the pressure of the air flow blown through the nozzle N (see FIG. 5(C)). The pressure signal Vg is supplied to the sampling/holding circuit 25 via the amplifier 24. The sampling/holding circuit 25 will repetitively take samples of the pressure signal only when the output signal level from the peak detecting circuit 22 is high, and it will hold the last taken sample when the output signal level from the peak detecting circuit 22 becomes lower than the last detected value. (see FIG. 5 (D)). The sample value of the pressure signal Vs held by the sampling-/holding circuit 25 is converted into a digital signal by the analog-to-digital converter 26 upon completion of the measuring process. The intraocular pressure is determined from the value of the digital signal by means of a processing circuit (not shown) using a predetermined correlation equation which relates the output signal values from the pressure detector with the intraocular pressure.

Since the intraocular pressure is determined from the air pressure which has actually been measured at the point of time when the cornea becomes flat, it is possible to determine the intraocular pressure with improved accuracy. Thus, unlike the prior art, measurements thus obtained by the present invention will not include significant errors which vary from one measurement to another. Moreover, the above-described air-puff tonometer is of a simple construction comprising a relatively small number of components such as the flattening detecting circuit 21, peak detecting circuit 22, pressure detector 23 and sampling/holding circuit 25, which means that it can be manufactured at low costs.

THIRD EMBODIMENT

Figure 6:
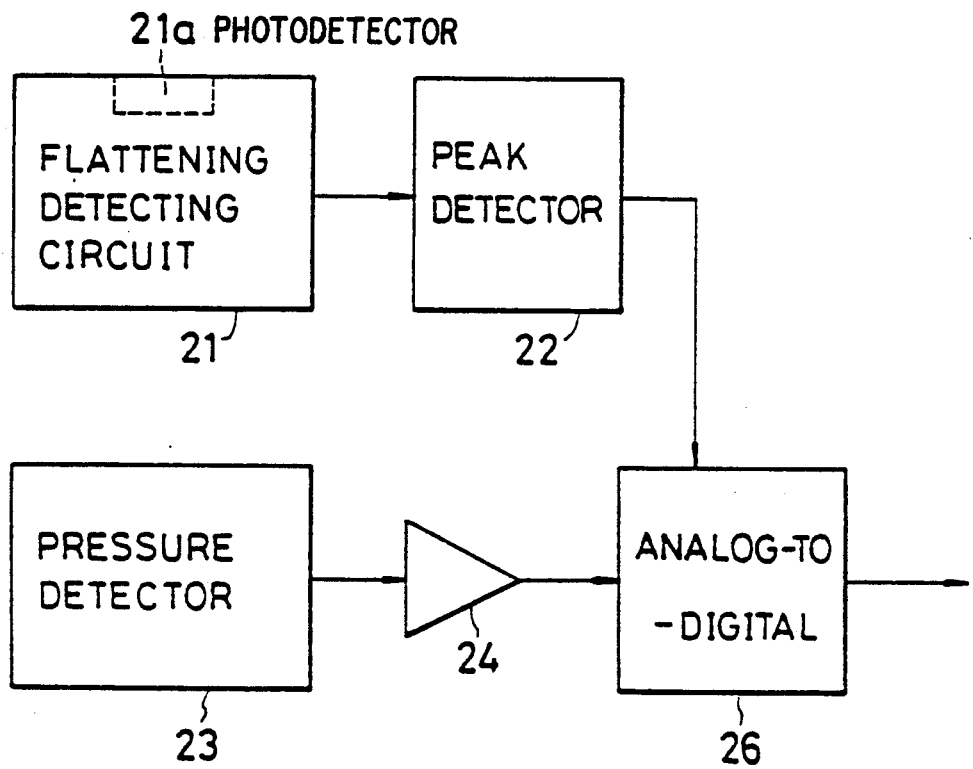
FIG. 6 is an illustration showing a third embodiment.

FIG. 6 shows a third embodiment of the invention to achieve the previously mentioned first and third objects. The apparatus of FIG. 6 differs from the apparatus of FIG. 3 in that it lacks the sampling/holding circuit 25 shown in FIG. 3 and that the analog-to-digital converter 26 can operate at a very high speed and will operate each time the signal level from the peak detector 22 turns high. The result of the last analog-to-digital conversion corresponds to the intraocular pressure.

What is claimed is:

1. In an air-puff tonometer, an apparatus for generating an air-puff comprising:
   a cylinder;
   a piston reciprocably disposed in said cylinder, said cylinder having a gas disposed therein;
   a nozzle disposed at one end of said cylinder;
   means for driving said piston to pressurize said gas in said cylinder thereby ejecting pressurized gas through said nozzle toward an eye being examined;
   electric current generating means for powering said driving means;
   pressure detecting means for detecting the pressure of said gas in said cylinder and for generating a pressure signal corresponding to said detected pressure; and
   current control means for controlling said current generating means, said current control means including means for comparing said pressure signal with a predetermined reference signal and for controlling the current supplied to said driving means such that a difference between said pressure signal and said reference signal is reduced.

2. The apparatus of claim 1, wherein said current control means further includes reference wave voltage generating circuit means for generating said reference signal in the form of a reference wave voltage signal having a waveform corresponding to a pressure signal waveform produced by said pressure detecting means when the pressure within said cylinder changes in an ideal manner during the compression stroke of the piston, and said comparing means includes error amplifying circuit means for comparing said pressure signal with said reference wave voltage signal and for producing a difference signal which corresponds to the difference between said pressure signal and said reference wave voltage signal; and
   current control circuit means for controlling the current supplied to said driving means through said electric current generating means in such a manner that said difference signal will be reduced substantially to zero.

3. The apparatus of claim 1, in which said pressure detecting means comprises a strain-gauge type pressure detector.

4. An air-puff tonometer, comprising:
   a cylinder;
   a piston reciprocably disposed in said cylinder, said cylinder having a gas disposed therein;
   a nozzle disposed at one end of said cylinder;
   means for driving said piston to pressurize said gas in said cylinder thereby ejecting pressurized gas through said nozzle toward an eye being examined;
   electric current generating means for powering said driving means;

pressure detecting means for detecting the pressure of said gas in said cylinder and for generating a pressure signal corresponding to said detected pressure;

current control means for controlling said current generating means, said current control means including means for comparing said pressure signal with a predetermined reference signal and for controlling the current supplied to said driving means such that a difference between said pressure signal and said reference signal will be reduced;

means for detecting flattening of the cornea of the eye being examined as a result of impingement by said pressurized gas; and means for detecting the pressure of air blown out through the nozzle upon detection of the flattening of the cornea by said flattening detecting means.

5. The air-puff tonometer as claimed in claim 4, in which said pressure detecting means is constituted by a strain-gauge type pressure detector.

6. The air-puff tonometer of claim 4, wherein said current control means further includes reference wave voltage generating circuit means for generating said reference signal in the form of a reference wave voltage signal having a waveform corresponding to a pressure signal waveform produced by said pressure detecting means when the pressure within said cylinder changes in an ideal manner during the compression stroke of the piston, and said comparing means includes error amplifying circuit means for comparing said pressure signal with said reference wave voltage signal and producing a difference signal which corresponds to the difference between said pressure signal and said reference wave voltage signal; and current control circuit means for controlling the current supplied to said driving means through said electric current generating means in such a manner that said difference signal will be reduced substantially to zero.

* * * * *